US006641583B2

(12) United States Patent
Shluzas et al.

(10) Patent No.: US 6,641,583 B2
(45) Date of Patent: Nov. 4, 2003

(54) APPARATUS FOR RETAINING BONE PORTIONS IN A DESIRED SPATIAL RELATIONSHIP

(75) Inventors: Alan E. Shluzas, Millis, MA (US); Gene P. DiPoto, Upton, MA (US)

(73) Assignee: Endius Incorporated, Plainville, MA (US)

(*) Notice: Subject to any disclaimer, the term of this patent is extended or adjusted under 35 U.S.C. 154(b) by 99 days.

(21) Appl. No.: 09/821,666

(22) Filed: Mar. 29, 2001

(65) Prior Publication Data

US 2002/0143328 A1 Oct. 3, 2002

(51) Int. Cl.[7] .............................................. A61B 17/70
(52) U.S. Cl. ....................................... 606/61; 606/69
(58) Field of Search ........................ 606/60, 61, 69–73

(56) References Cited

U.S. PATENT DOCUMENTS

| 4,836,196 A | | 6/1989 | Park et al. |
| 5,234,431 A | | 8/1993 | Keller |
| 5,501,684 A | | 3/1996 | Schlapfer et al. |
| 5,531,745 A | * | 7/1996 | Ray ............................ 606/61 |
| 5,575,791 A | | 11/1996 | Lin |
| 5,582,612 A | | 12/1996 | Lin |
| 5,613,967 A | | 3/1997 | Engelhardt et al. |
| 5,613,968 A | | 3/1997 | Lin |
| 5,672,176 A | | 9/1997 | Biedermann et al. |
| 5,728,127 A | * | 3/1998 | Asher et al. ................. 606/61 |
| 5,891,145 A | | 4/1999 | Morrison et al. |
| 5,902,303 A | | 5/1999 | Eckhof et al. |
| 6,066,140 A | * | 5/2000 | Gertzbein et al. ............ 606/61 |
| 6,080,156 A | | 6/2000 | Asher et al. |
| 6,280,443 B1 | | 8/2001 | Gu et al. |
| 6,280,445 B1 | * | 8/2001 | Morrison et al. ............. 606/61 |
| 6,287,309 B1 | * | 9/2001 | Baccelli et al. ............. 606/61 |
| 6,302,883 B1 | * | 10/2001 | Bono ........................... 606/69 |
| 6,315,779 B1 | * | 11/2001 | Morrison et al. ............. 606/69 |
| 6,432,108 B1 | * | 8/2002 | Burgess et al. .............. 606/61 |

\* cited by examiner

*Primary Examiner*—Kevin Shaver
*Assistant Examiner*—Michael B. Priddy
(74) *Attorney, Agent, or Firm*—Tarrolli, Sundheim, Covell & Tummino L.L.P.

(57) ABSTRACT

An apparatus (10) includes a member (12) having an elongate slot (50). A fastener (16) engageable with a bone portion has an end portion (26) extending through the elongate slot (50). A connecting ring (42) connects the member (12) to the fastener (16). The connecting ring (42) is positionable in any one of a plurality of positions along the elongate slot (50). The connecting ring (42) has a passage (54) through which the end portion (26) of the fastener (16) extends. The fastener (16) is positionable in any one of a plurality of angular positions relative to the connecting ring (42). First and second portions (64, 66) of the connecting ring (42) engage each other to connect the first and second portions together and prevent relative movement between the first and second portions. A clamping member (28) engages the end portion (26) of the fastener (16) and the connecting ring (42) to connect the connecting ring to the member (12) in any one of the plurality of positions relative to the member and connect the fastener (16) in any one of the plurality of angular positions relative to the connecting ring (42).

60 Claims, 5 Drawing Sheets

APPARATUS FOR RETAINING BONE PORTIONS IN A DESIRED SPATIAL RELATIONSHIP

TECHNICAL FIELD

The present invention relates to an apparatus which is used to retain bone portions, such as vertebrae of a spinal column, in a desired spatial relationship.

BACKGROUND OF THE INVENTION

A known apparatus for retaining vertebrae of a spinal column in a desired spatial relationship is disclosed in U.S. Pat. No. 5,613,968. U.S. Pat. No. 5,613,968 discloses an apparatus including a longitudinal member extendable along the spinal column. A fixation member connects the longitudinal member to a fastener connectable with a vertebra. A universal pad connects the fastener with the fixation member. The universal pad extends into the fixation member and the fastener extends through the universal pad. The universal pad has a protruding arcuate surface and a recessed arcuate surface concentric with the protruding arcuate surface. A clamping member is provided with a recessed arcuate surface engageable with the protruding arcuate surface on the universal pad. The fastener has a protruding arcuate surface engaging a recessed arcuate surface on the universal pad. The fastener is universally pivotable in any direction relative to the universal pad.

SUMMARY OF THE INVENTION

The present invention is an apparatus which is used to retain bone portions in a desired spatial relationship. The apparatus includes a member connectable with a bone portion having an elongate slot. A fastener connects the member to the bone portion and has a longitudinal axis. The fastener has a first end portion engageable with the bone portion and a second end portion extending through the elongate slot in the member.

A connecting ring connects the member to the fastener. The connecting ring extends into the elongate slot in the member and is positionable in any one of a plurality of positions along the elongate slot relative to the member. The connecting ring has a passage with a longitudinal axis through which the second end portion of the fastener extends. The fastener is positionable in any one of a plurality of angular positions relative to the connecting ring so that the longitudinal axis of the fastener extends at any one of a plurality of angles to the longitudinal axis of the passage in the connecting ring.

The connecting ring has first and second portions engageable with each other to connect the connecting ring to the member. The first and second portions of the connecting ring engage each other to connect the first and second portions together and prevent relative movement between the first and second portions. A clamping member engages the second end portion of the fastener and the connecting ring to connect the connecting ring to the member in any one of the plurality of positions relative to the member and connect the fastener in any one of the plurality of angular positions relative to the connecting ring.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF THE INVENTION

The present invention is directed to an apparatus for retaining bone portions, such as vertebrae of a spinal column, in a desired spatial relationship. FIGS. 1–4 illustrate an apparatus 10 constructed according to a first embodiment of the present invention. The apparatus 10 (FIGS. 1 and 2) includes a surgically implantable longitudinal plate or member 12 for maintaining bone portions, such as vertebrae V of a spinal column, in a desired spatial relationship. The member 12 (FIG. 2) is connected with vertebrae V of the spinal column by fasteners 16. Also, the plate 12 may be used to maintain bone portions, such as bone portions of a broken bone, in a desired spatial relationship.

The member or plate 12 is connected to respective vertebrae V by the fasteners 16 made of suitable biocompatible material. Each of the fasteners 16 has a threaded inner end portion 22 having a course thread convolution 24 which engages the vertebrae V. An outer end portion 26 (FIG. 3) of the fastener 16 is provided with a relatively fine thread which engages an internal thread convolution on a clamping member or nut 28 made of a suitable biocompatible material.

Wrenching flats 30 are provided on the end portion 26 of the fastener 16. Torque is applied to these flats 30 to turn the thread convolution 24 into the vertebra V. An intermediate portion 32 of the fastener 16 has wrenching flats 34. Torque may be applied to the wrenching flats 34 to turn the thread convolution 24 into the vertebra V. The intermediate portion 32 of a fastener 16 has an arcuate convex surface 40 (FIGS. 2 and 3) which abuttingly engages a connecting ring 42. When the clamping member 28 is tightened, the connecting ring 42 is securely clamped against the surface 40 of the intermediate portion 32 to connect the member 12 to the fastener 16.

The plate 12 has a length which is at least sufficient to enable the plate to span at least two vertebrae V. In the embodiment of the invention illustrated in FIGS. 1–4, the plate 12 spans two vertebrae V. Of course, the length of the plate 12 in any particular installation will depend upon the condition to be corrected and the number of vertebrae V to be held in a desired spatial relationship relative to each other by the plate.

The plate 12 (FIGS. 1–3) includes an elongate slot 50 through which the outer end portion 26 of one of the fasteners 16 extends. The plate 12 also includes an elongate keyhole slot 52 through which the outer end portion 26 of another fastener 16 extends. The connecting ring 42 extends through the elongate slot 50 in the plate 12 to connect the plate to the fastener 16. The connecting ring 42 is positionable in any one of a plurality of positions along the elongate slot 50 relative to the plate 12.

The connecting ring 42 (FIGS. 2–4) has a passage 54 with a longitudinal axis 56 through which the outer end portion 26 of the fastener 16 extends. The fastener 16 (FIGS. 1 and 2) is positionable in any one of a plurality of angular positions relative to the connecting ring 42 so that a longitudinal axis 58 of the fastener extends at any one of a plurality of angles to the longitudinal axis 56 of the passage 54 in the connecting ring. More specifically, the fastener 16 is universally pivotable in any direction relative to the connecting ring 42.

The connecting ring 42 (FIGS. 2–4) has a first or upper portion 64 and a second or lower portion 66 engageable with each other to connect the connecting ring 42 to the member 12. The lower portion 66 (FIGS. 3 and 4) of the connecting ring 42 has an axially extending portion 68. The axially extending portion 68 of the lower portion 66 extends into an opening 70 in the upper portion 64 of the connecting ring 42. A cylindrical outer surface 74 on the axially extending portion 68 frictionally engages a cylindrical surface 78 defining the opening 70. There is an interference fit between the axially extending portion 68 and the surface 78 defining the opening 70 to connect the upper and lower portions 64 and 66 to each other.

Figure 2:
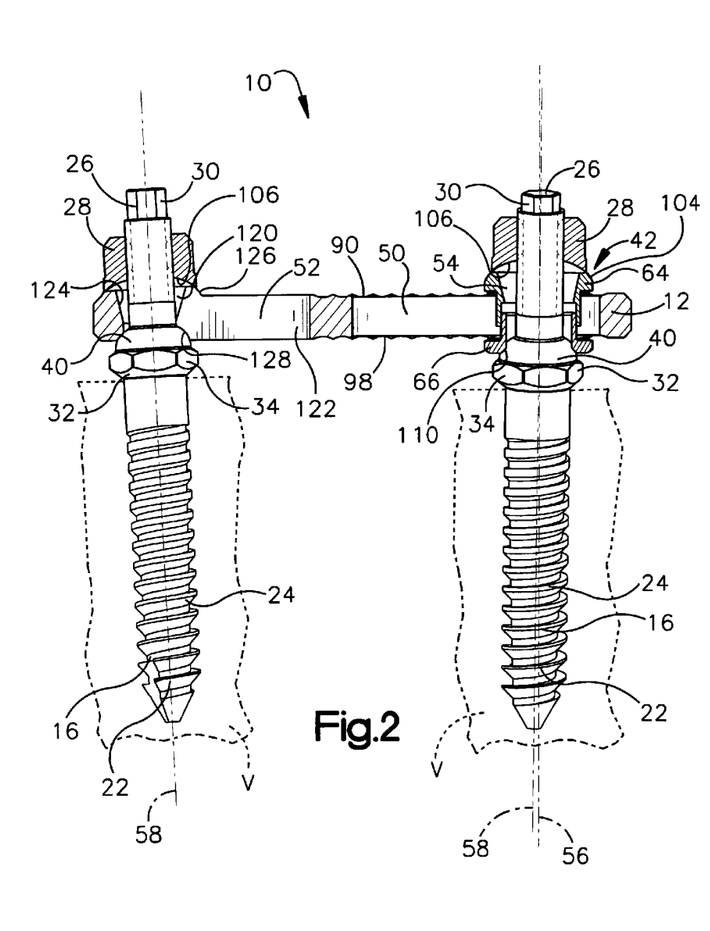
FIG. 2 is a sectional view of the apparatus of FIG. 1 showing the apparatus interconnecting bone portions.
Figures 3, 4:
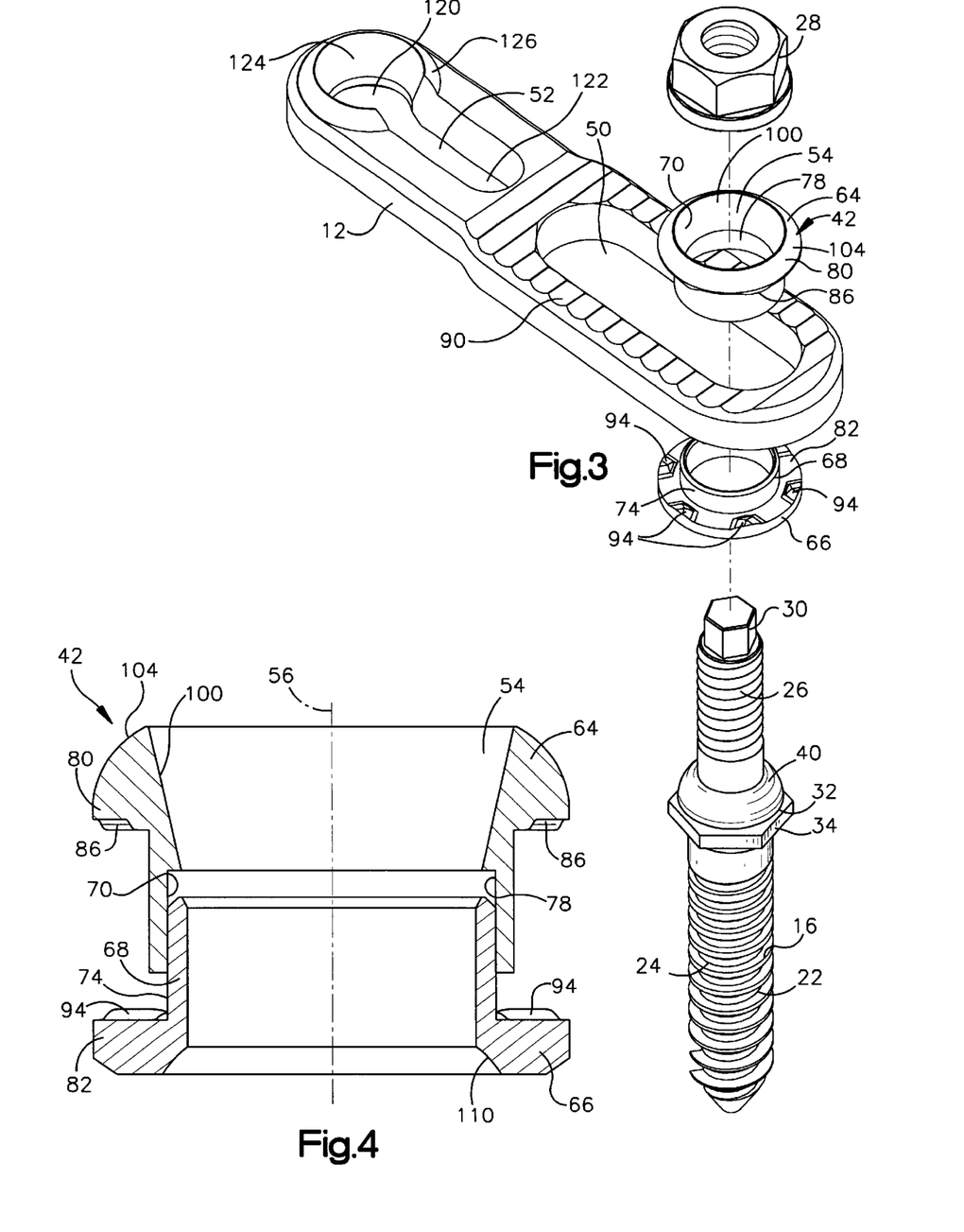
FIG. 3 is an exploded perspective view of a portion of the apparatus of FIG. 1.
FIG. 4 is an enlarged sectional view of a connecting ring of the apparatus of FIG. 1.

The connecting ring 42 is connected to the plate 12 by extending the upper and lower portions 64 and 66 into the slot 50 into engagement with each other. The upper and lower portions 64 and 66 are moved axially relative to each other until the upper and lower portions are connected to each other and the connecting ring 42 is movable along the slot 50. The connecting ring 42 is positioned along the slot 50 in any one of the plurality of positions along the slot. Then the second end portion 26 of the fastener 16 is placed through the passage 54 in the connecting ring 42 with the lower portion 66 engaging the intermediate portion 32 of the fastener. The fastener 16 is pivotally moved relative to the connecting ring 42 into any one of the plurality of pivot positions relative to the connecting ring.

The clamping member 28 is threaded onto the fastener and engages the upper portion 64 of the connecting ring 42. The clamping member 28 applies an axially directed force to the upper portion 64 to further move the upper portion axially relative to the lower portion 66 and connect the connecting ring 42 in any one of the plurality of positions along the slot 50. The clamping member 28 also connects the fastener 16 in any one of the plurality of angular positions relative to the connecting ring 42.

The upper portion 64 (FIGS. 3 and 4) of the connecting ring 42 has a radially extending flange 80 engageable with the plate 12. The lower portion 66 of the connecting ring 42 has a radially extending flange 82 engageable with the plate 12. The flange 80 on the upper portion 64 has axially extending projections 86 engageable with grooves 90 on the member 12. The flange 82 on the lower portion 66 has axially extending projections 94 engageable with grooves 98 (FIG. 2) on the member 12. The grooves 90 and 98 on the member 12 extend transverse to a longitudinal axis of the plate 12 and the elongate slot 50.

The projections 86 and 94 on the connecting ring 42 engage the grooves 90 and 98 on the member 12 to prevent rotation of the connecting ring relative to the member when the clamping member 28 engages the connecting ring. It is contemplated that the member 12 could have grooves on only one side and that only one of the upper and lower portions 64 and 66 could have projections. It is also contemplated that the member 12 could have no grooves and the connecting ring 42 no projections.

The upper portion 64 (FIGS. 3 and 4) of the connecting ring 42 includes a tapered surface 100 defining the passage 54 in the connecting ring. The upper portion 64 has an arcuate convex surface 104. The surface 104 on the upper portion 64 engages an arcuate concave surface 106 (FIG. 2) on the nut 28. The lower portion 66 (FIGS. 2–4) of the connecting ring 42 has an arcuate concave surface 110. The surface 110 on the portion 66 engages the arcuate convex surface 40 on the intermediate portion 32 of the fastener 16. Accordingly, the fastener 16 is universally pivotable in any direction relative to the connecting ring 42.

The keyhole slot 52 (FIGS. 1–3) has an end 120 with a diameter larger than a width of the slot at an end 122. The end 120 is defined by a tapered surface 124. The plate 12 has an arcuate convex surface 126 adjacent to the end 120 of the slot 52. The plate 12 (FIG. 2) also has an arcuate concave surface 128 adjacent to the end 120. The arcuate surface 126 on the plate 12 engages the arcuate concave surface 106 on the nut 28. The arcuate surface 128 on the member 12 engages the arcuate convex surface 40 on the fastener 16. Accordingly, the fastener 16 is universally pivotable relative to the member 12 adjacent the end 120 of the slot 52.

Figure 1:
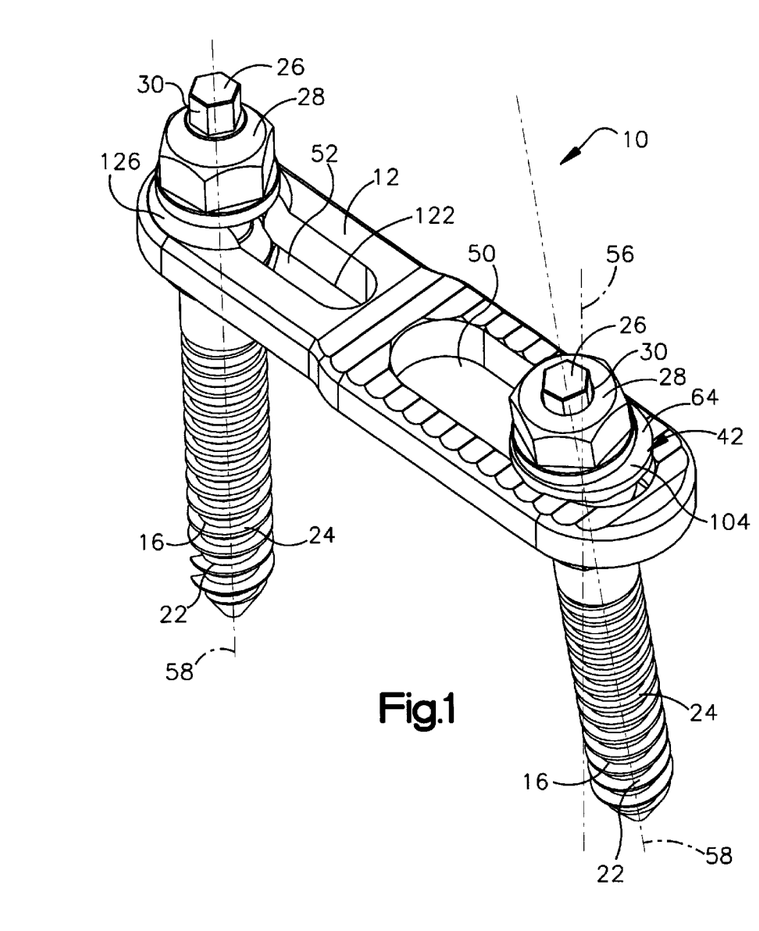
FIG. 1 is a perspective view of an apparatus constructed in accordance with a first embodiment of the present invention.

When the plate 12 is to be connected to the vertebrae V of the spinal column, the fasteners 16 are connected to the vertebrae. The connecting ring 42 is connected to the plate 12 extending through the slot 50 in the plate so that the connecting ring is positionable along the slot 50. The connecting ring 42 is positioned in any one of the plurality of positions along the slot 50. The plate 12 is placed on the fasteners 16. The plate 12 is positioned with one of the fasteners 16 extending through the end 120 of the keyhole slot 52 and the other fastener 16 extending through the connecting ring 42. The fasteners 16 are positioned in any one of the plurality of angular positions relative to the connecting ring 42 and the plate 12.

Once the plate 12 has been positioned relative to the fasteners 16, clamping members 28 are placed on the fasteners. The clamping members 28 are threaded onto the fasteners 16. One of the clamping members 28 connects the fastener 16 extending through the slot 52 to the plate 12. The other clamping member 28 causes the upper and lower portions 64 and 66 of the connecting ring 42 to move axially relative to each other. The upper and lower portions 64 and 66 of the connecting ring 42 move relative to each other until the plate 12 is clamped between the upper and lower portions of the connecting ring. The nut 28 also clamps the connecting ring 42 to the intermediate portion 32 of the fastener 16.

Figure 5:
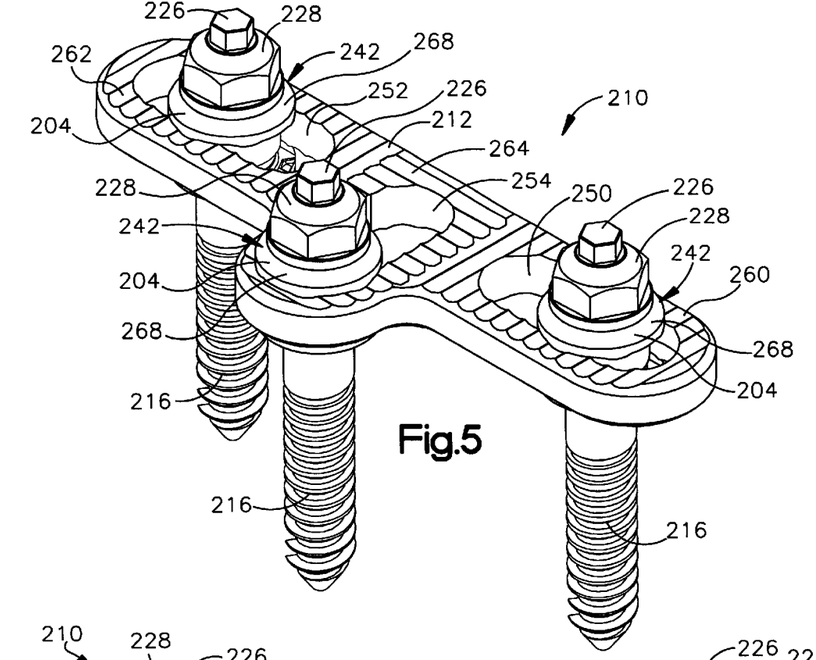
FIG. 5 is a perspective view of an apparatus constructed in accordance with a second embodiment of the present invention.
Figure 6:
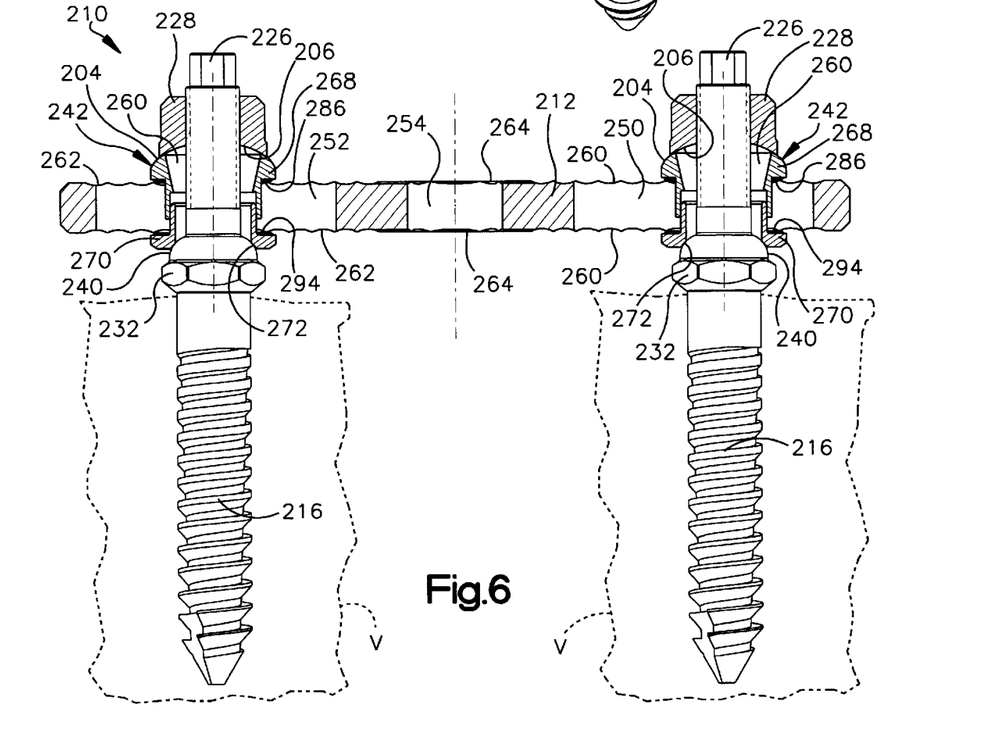
FIG. 6 is a sectional view of the apparatus of FIG. 5 showing the apparatus connected to bone portions.

An apparatus 210 constructed according to a second embodiment of the present invention is illustrated in FIGS. 5 and 6. The apparatus 210 includes a surgically implantable T-shaped plate or member 212 for maintaining bone portions, such as vertebrae of spinal column, in a desired spatial relationship. The plate 212 is connected to respective vertebrae V by fasteners 216 made of a suitable biocompatible material. Each of the fasteners 216 is identical to the fasteners 16 described in connection with the embodiment disclosed in FIGS. 1–4. Accordingly, the fasteners 216 will not be described in detail. The plate 212 has three elongate slots 250, 252, and 254 through which outer end portions 226 of the fasteners 216 extend. The slot 254 extends transverse to the slots 250 and 252.

The fasteners 216 are connected to the plate 212 by connecting rings 242. The connecting rings 242 are positionable along the slots 250, 252, and 254 in any one of a plurality of positions relative to the plate 212. The connecting rings 242 are identical to the connecting rings 42 described in connection with the embodiment disclosed in FIGS. 1–4. Accordingly, the connecting rings 242 will not be described in detail.

Each of the connecting rings 242 (FIG. 6) has projections 286 and 294 to prevent the connecting rings from rotating relative to the plate 212 when clamping members 228 engage the connecting rings. The projections 286 and 294 on the connecting ring 242 that extends through the elongate slot 250 engages grooves 260 on opposite sides of the plate 212. The grooves 260 extend transverse to the longitudinal axis of the slot 250. The projections 286 and 294 on the connecting ring 242 extending through the elongate slot 252 engage grooves 262 on opposite sides of the plate 212. The grooves 262 extend transverse to a longitudinal axis of the slot 252. The projections on the connecting ring 242 extending through the elongate slot 254 engage grooves 264 on opposite sides of the plate 212. The grooves 264 extend transverse to a longitudinal axis of the slot 254.

It is contemplated that the plate 212 could have grooves on only one side and that only one of the upper and lower portions 268 and 270 of the connecting rings 242 could have projections. It is also contemplate that the plate 212 could have no grooves and that the connecting rings could have no projections.

The connecting rings 242 (FIGS. 5 and 6) are positionable in any one of a plurality of positions along the elongate slots 250, 252, and 254 relative to the member 212. The connecting rings 242 have passages 260 with longitudinal axes through which the second end portions 226 of the fasteners 216 extend. The fasteners 216 are positionable in any one of a plurality of angular positions relative to the connecting rings 242 so that the longitudinal axes of the fasteners extend at any one of plurality of angles to the longitudinal axes of the passages 260 in the connecting rings. The fasteners 216 are universally pivotable in any direction relative to the connecting rings 242.

The upper portions 268 of the connecting rings 242 have arcuate convex surfaces 204. The arcuate surfaces 204 (FIG. 6) on the upper portions 268 engage arcuate concave surfaces 206 on the clamping members 228. The lower portions 270 of the connecting rings 242 have arcuate concave surfaces 272. The arcuate surfaces 272 on the lower portions 270 engage arcuate convex surfaces 240 on intermediate portions 232 of the fasteners 216. Accordingly, the fasteners 216 are universally pivotable relative to the connecting rings 242.

When the plate 212 is to be connected to the vertebrae V, the fasteners 216 are connected to the vertebrae. The connecting rings 242 are connected to the plate 212 so that the connecting rings may be positioned along the slots 250, 252, and 254 relative to the plate. After the connecting rings 242 are positioned relative to the plate 212, the plate is placed on the fasteners 216 with the fasteners extending through the connecting rings. The fasteners 216 are positioned in any one of the plurality of angular positions relative to the connecting rings 242.

Once the plate 212 has been positioned relative to the fasteners 216, the clamping members 228 are placed on the fasteners. The clamping members 228 are threaded onto the fasteners 216 to cause the upper and lower portions 268 and 270 of the connecting rings 242 to move axially relative to each other and clamp the plate 212 between the upper and lower portions. The nuts 228 also clamp the connecting rings 242 to the intermediate portions 232 of the fasteners 216.

Figures 7, 8:
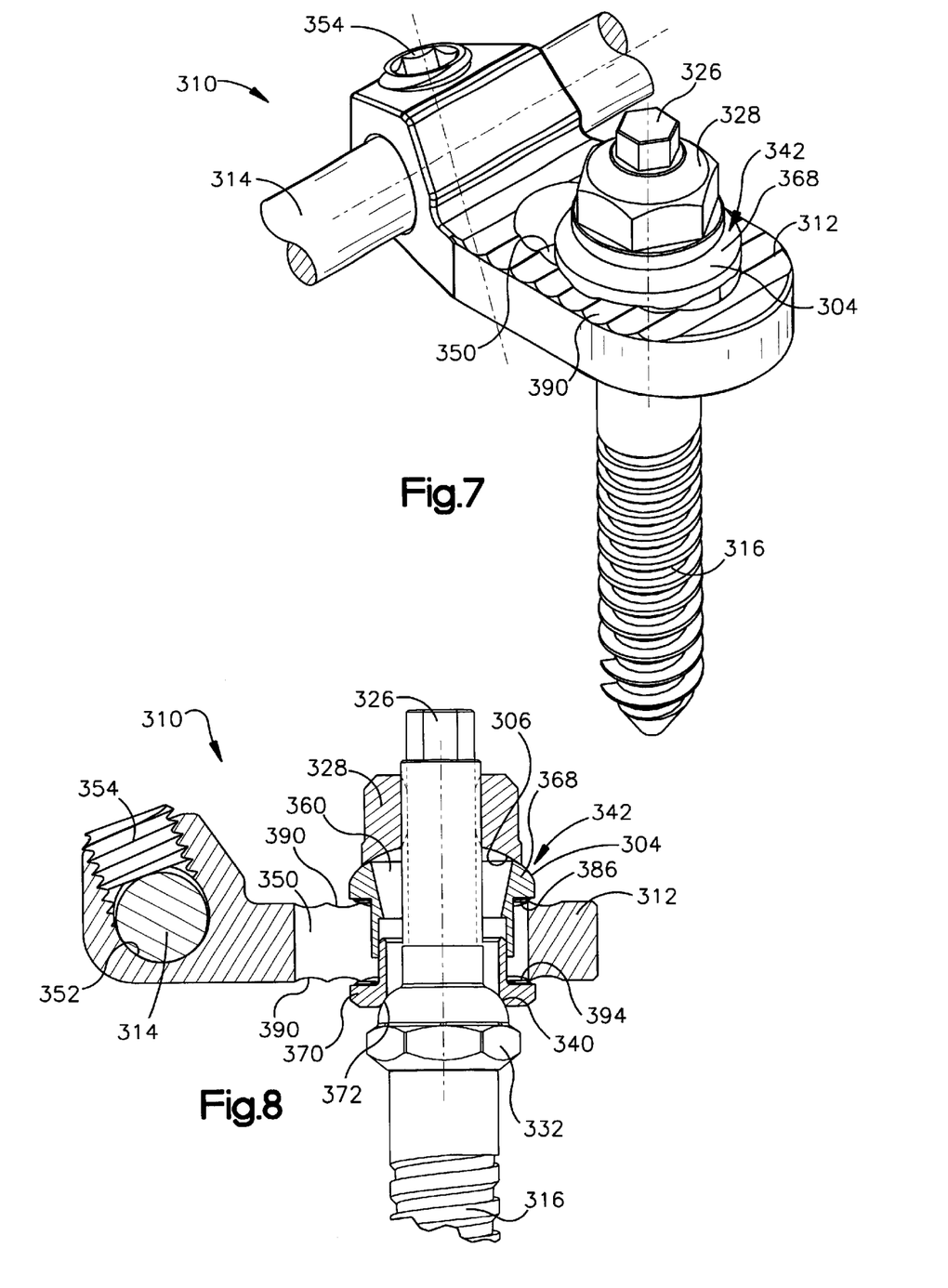
FIG. 7 is a perspective view of an apparatus constructed in accordance with a third embodiment of the present invention.
FIG. 8 is a sectional view of the apparatus of FIG. 7.

An apparatus 310 constructed in accordance with a third embodiment of the present invention is illustrated in FIGS. 7 and 8. The apparatus 310 includes a surgically implantable member 312 for maintaining bone portions, such as vertebrae of a spinal column, in a desired spatial relationship. The member 312 connects a spinal rod 314 extending along the spinal column to the vertebra.

The spine rod 314 and member 312 are connected to a respective vertebra by a fastener 316. The fastener 316 is identical to the fasteners 16 described in connection with the embodiment illustrated in FIGS. 1–4. Accordingly, the fastener 316 will not be described in detail. The member 310 has an elongate slot 350 through which an outer end portion 326 of the fastener 316 extends.

The fastener 316 is connected to the member 312 by a connecting ring 342. The connecting ring 342 is positionable along the slot 350 in any one of a plurality of positions relative to the member 312. The connecting ring 342 is identical to the connecting ring 42 described in connection with the embodiment illustrated in FIGS. 1–4. Accordingly, the connecting ring 342 will not be described in detail.

The connecting ring 342 extends through the elongate slot 350 in the member 312. The connecting ring 342 (FIG. 8) has projections 386 and 394 engageable with grooves 390 on opposite sides of the member 312. The projections 386 and 394 prevent rotation of the connecting ring 342 relative to the member 312 when a clamping member 328 engages the connecting ring. The grooves 390 extend transverse to a longitudinal axis of the elongate slot 350. It is contemplated that the member 312 could have grooves on only one side and that only one of the upper and lower portions 368 and 370 could have projections. It is also contemplated that the member 312 could have no grooves and the connecting ring 342 no projections.

The spine rod 314 extends through a passage 352 in the member 312. The elongate slot 350 extends transverse to the passage 352. A set screw or fastener 354 threadably engages the member 312 to clamp the spine rod 314 in the passage 352.

The connecting ring 342 is positionable in any one of a plurality of positions along the slot 350 relative to the member 312. The connecting ring 342 has a passage 360 with a longitudinal axis through which the second end portion 326 of the fastener 316 extends. The fastener 316 is positionable in any one of a plurality of angular positions relative to the connecting ring 342 so that the longitudinal axis of the fastener extends at any one of a plurality of angles relative to the longitudinal axis of the passage 360 in the connecting ring. The fastener 316 is universally pivotable in any direction relative to the connecting ring 342.

The upper portion 368 of the connecting ring 342 has an arcuate convex surface 304. The arcuate surface 304 engages an arcuate concave surface 306 on the clamping member 328. The lower portion 370 of the connecting ring 342 has an arcuate concave surface 372. The arcuate surface 372 on the lower portion 370 engages an arcuate convex surface 340 on an intermediate portion 332 of the fastener 316. Accordingly, the fastener 316 is universally pivotable relative to the connecting ring 342.

When the spine rod 314 is to be connected to a vertebra, the fastener 316 is connected to the vertebra. The connecting ring 342 is connected to the member 312 so that the connecting ring can be positioned along the elongate slot 350. After the connecting ring 342 is positioned relative to the member 312, the member is placed on the rod 314 and the fastener 316 with the fastener extending through the connecting ring 342. The fastener 316 is positioned in any one of the plurality of angular positions relative to the connecting ring 342.

Once the member 312 has been positioned relative to the fastener 316, the clamping member 328 is placed on the fastener. The clamping member 328 is threaded onto the fastener 316 to cause the upper and lower portions 368 and 370 of the connecting ring 342 to move axially relative to each other until the member 312 is clamped between the upper and lower portions. The clamping member 328 also clamps the connecting ring 342 to the intermediate portion 332 of the fastener 316. The set screw 354 is threaded into the member 312 to clamp the spine rod 314 to the member.

Figures 9, 10:
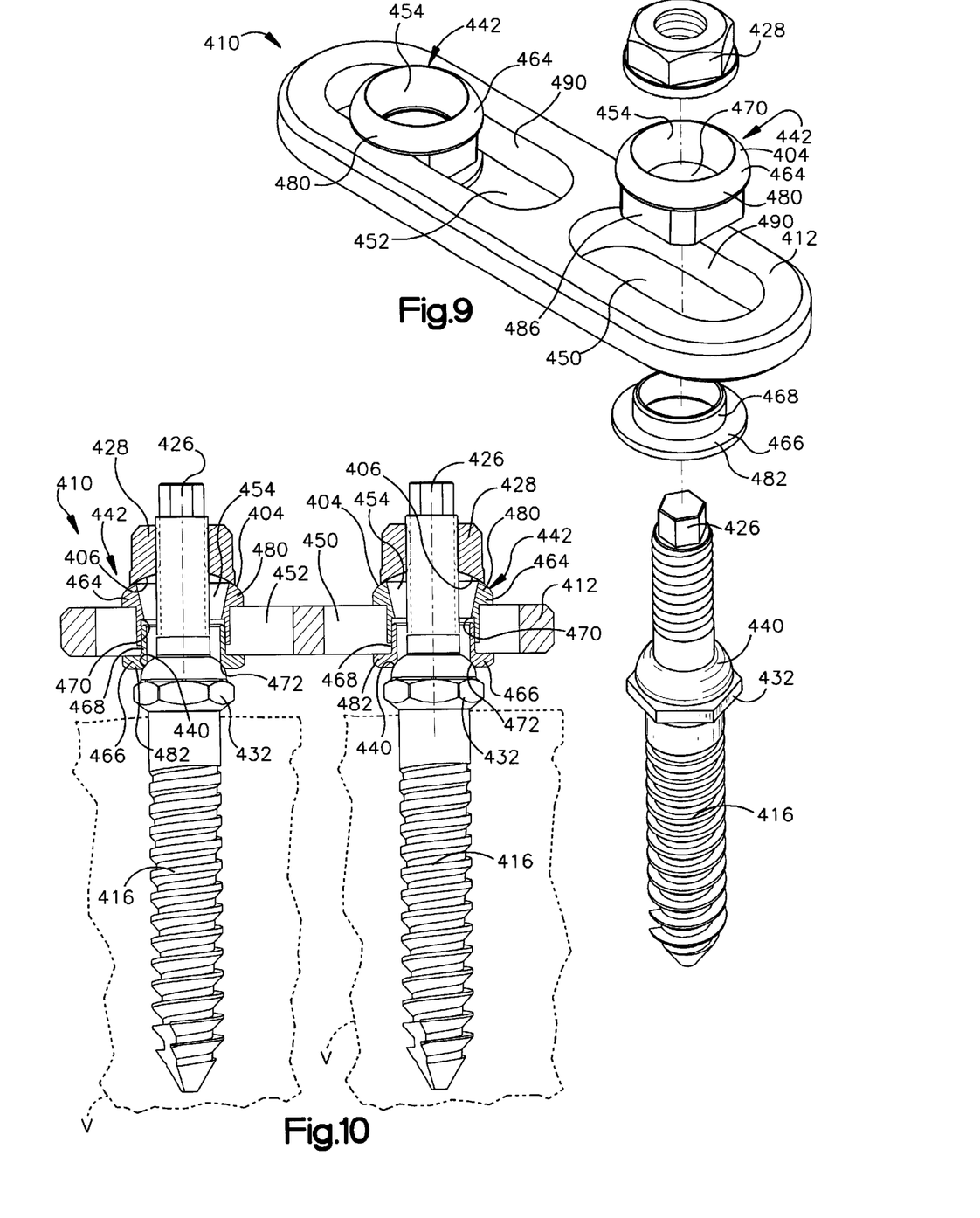
FIG. 9 is a perspective view of an apparatus constructed in accordance with a fourth embodiment of the present invention with a fastener removed for clarity.
FIG. 10 is a sectional view of the apparatus of FIG. 9 showing the apparatus connected to bone portions.

An apparatus 410 constructed according to a fourth embodiment of the present invention is illustrated in FIGS. 9 and 10. The apparatus 410 includes a surgically implantable plate or member 412 for maintaining bone portions, such as vertebrae V of a spinal column, in a desired spatial relationship. The member 412 is connected to the vertebrae V of the spinal column by fasteners 416. The fasteners 416 are identical to the fastener 16 described in connection with the embodiment illustrated in FIGS. 1–4. Accordingly, the fasteners 416 will not be described in detail. The member 412 has elongate slots 450 and 452 through which outer end portions 426 of the fasteners 416 extend.

The fasteners 416 are connected to the plate 412 by connecting rings 442. The connecting rings 442 extend through the elongate slots 450 and 452 in the plate 412. The connecting rings 442 are positionable in any one of a plurality of positions along the elongate slots 450 and 452 relative to the plate 412.

The connecting rings 442 have passages 454 through which the outer end portions 426 of the fasteners 416 extend. The fasteners 416 are positionable in any one of a plurality of angular positions relative to the connecting rings 442 so that longitudinal axes of fasteners extend at any one of a plurality of angles to the longitudinal axes of the passages 454 in the connecting rings. More specifically, the fasteners 416 are universally pivotable in any direction relative to the connecting rings 442.

The connecting rings 442 (FIGS. 9 and 10) have first or upper portions 464 and second or lower portions 466 engageable with each other to connect the connecting rings 442 to the member 412. The lower portion 466 of the connecting ring 442 has an axially extending portion 468. The axially extending portion 468 of the lower portion 466 extends into an opening 470 in the upper portion 464 of the connecting ring 442. There is an interference fit between the axially extending portion 468 and the upper portion 464 to connect the upper and lower portions 464 and 466 to each other.

The upper portions 464 of the connecting rings 442 have radially extending flanges 480 engageable with the plate 412. The lower portions 466 of the connecting rings 442 have radially extending flanges 482 engageable with the plate 412. The upper portions 464 have parallel surfaces 486, one of which is shown in FIG. 9, engageable with parallel surfaces 490 on the member 412. The surfaces 490 define the slots 450 and 452. The surfaces 486 on the connecting rings 442 engage the surfaces 490 on the member 412 to prevent rotation of the connecting rings 442 relative to the member.

The upper portions 464 of the connecting rings 442 have arcuate convex surfaces 404. The arcuate surfaces 404 on the upper portions 464 engage arcuate concave surfaces 406 on clamping members 428. The lower portions 460 of the connecting rings 442 have arcuate concave surfaces 472. The arcuate surfaces 472 on the lower portions 466 engage arcuate convex surfaces 440 on intermediate portions 432 of the fasteners 416. Accordingly, the fasteners 416 are universally pivotable relative to the connecting rings 442.

When the plate 412 is to be connected to the vertebrae V, the fasteners 416 are connected to the vertebrae. The connecting rings 442 are connected to the plate 412 so that the connecting rings may be positioned along the slots 450 and 452 relative to the plate. After the connecting rings 442 are positioned relative to the plate 412, the plate is placed on the fasteners 416 with the fasteners extending through the connecting rings. The fasteners 416 are positioned in any one of the plurality of angular positions relative to the connecting rings 442.

Once the plate 412 has been positioned relative to the fasteners 416, the clamping members 428 are placed on the fasteners. The clamping members 428 are threaded onto the fasteners 416 to cause the upper and lower portions 464 and 466 of the connecting rings 442 to move axially relative to each other and clamp the plate 412 between the upper and lower portions. The nuts 428 also clamp the connecting rings 442 to the intermediate portions 431 of the fasteners 416.

Although the clamping members of the present invention are shown with arcuate concave surfaces engageable with arcuate convex surfaces on the connecting rings, it is contemplated that the clamping members could have convex surfaces engageable with concave surfaces on the connecting rings. Furthermore, it is contemplated that the fasteners could have arcuate concave surface engageable with arcuate convex surfaces on the connecting rings.

From the above description of the invention, those skilled in the art will perceive improvements, changes and modifications. Such improvements, changes and modifications within the skill of the art are intended to be covered by the appended claims.

Having described the invention, the following is claimed:

1. An apparatus comprising:

a member connectable with a bone portion, said member having an opening;

a fastener for connecting said member to the bone portion having a longitudinal axis, said fastener having a first end portion engageable with the bone portion and a second end portion extending through said opening in said member;

a connecting ring for connecting said member to said fastener, said connecting ring extending into said opening in said member, said connecting ring having a passage with a longitudinal axis through which said second end portion of said fastener extends, said fastener being positionable in any one of a plurality of angular positions relative to said connecting ring so that said longitudinal axis of said fastener extends at any one of a plurality of angles to said longitudinal axis of said passage in said connecting ring, said connecting ring having first and second portions engageable with each other to connect said connecting ring to said member, said first and second portions of said connecting ring engaging each other to connect said first and second portions together and prevent relative movement between said first and second portions; and a clamping member engaging said second end portion of said fastener and said connecting ring to connect said connecting ring to said member and connect said fastener to said connecting ring in any one of said plurality of angular positions relative to said connecting ring.

2. An apparatus as defined in claim 1 wherein said fastener is universally pivotable in any direction relative to said connecting ring prior to said clamping member connecting said fastener to said connecting ring.

3. An apparatus as defined in claim 1 wherein said clamping member applies a force to said connecting ring to move said first portion relative to said second portion, said first and second portions moving into engagement with said member to prevent movement of said connecting ring relative to said member.

4. An apparatus as defined in claim 1 wherein said connecting ring has surfaces engageable with surfaces on said member to prevent rotation of said connecting ring relative to said member.

5. An apparatus as defined in claim 4 wherein said connecting ring has projections engageable with grooves on said member to prevent rotation of said connecting ring relative to said member.

6. An apparatus as defined in claim 5 wherein said grooves on said member extend transverse to a longitudinal axis of said member.

7. An apparatus as defined in claim 5 wherein each of said first and second portions of said connecting ring has projections engageable with grooves on said member to prevent rotation of said connecting ring relative to said member.

8. An apparatus as defined in claim 4 wherein said connecting ring has first and second surfaces extending parallel to each other, said member having first and second surfaces at least partially defining said opening and extending parallel to each other, said first and second surfaces on said connecting ring engaging said first and second surfaces defining said opening to prevent rotation of said connecting ring relative to said member.

9. An apparatus as defined in claim 1 wherein said first portion of said connecting ring has a tapered surface defining said passage through which said second end portion of said fastener extends.

10. An apparatus as defined in claim 9 wherein said first portion of said connecting ring has an arcuate surface engageable with an arcuate surface on said clamping member.

11. An apparatus as defined in claim 10 wherein said arcuate surface on said first portion is a convex surface and said arcuate surface on said clamping member is a concave surface.

12. An apparatus as defined in claim 10 wherein said fastener has an intermediate portion between said first and second end portions, said intermediate portion being engageable with said second portion of said connecting ring.

13. An apparatus as defined in claim 12 wherein said second portion has an arcuate surface engageable with an arcuate surface on said intermediate portion of said fastener.

14. An apparatus as defined in claim 13 wherein said arcuate surface on said second portion is concave and said arcuate surface on said intermediate portion of said fastener is convex.

15. An apparatus as defined in claim 1 wherein said second portion of said connecting ring extends into an opening in said first portion.

16. An apparatus as defined in claim 15 wherein said first and second portions of said connecting ring have an interference fit.

17. An apparatus as defined in claim 1 wherein said opening in said member is an elongate slot, said connecting ring being positionable in any one of a plurality of positions along said elongate slot relative to said member prior to said clamping member engaging said connecting ring.

18. An apparatus as defined in claim 1 further including a second fastener having a first end portion engageable with a bone portion and a second end portion and a second clamping member engageable with said second end portion and said member for connecting said second fastener to said member, said second end portion of said fastener extending through an elongate slot in said member, said second fastener being universally pivotable in any direction relative to an end of said elongate slot prior to said second clamping member engaging said member.

19. An apparatus as defined in claim 18 wherein said end of said elongate slot is defined by a tapered surface.

20. An apparatus as defined in claim 18 wherein said member includes an arcuate surface adjacent to said end of said elongate slot, said second clamping member having an arcuate surface engageable with said arcuate surface on said member.

21. An apparatus as defined in claim 20 wherein said arcuate surface on said member is convex and said arcuate surface on said second clamping member is concave.

22. An apparatus as defined in claim 18 wherein said second fastener includes an intermediate portion between said first and second end portions, said intermediate portion having an arcuate surface engageable with an arcuate surface on said member.

23. An apparatus as defined in claim 22 wherein said arcuate surface on said intermediate portion is convex and said arcuate surface on said member is concave.

24. An apparatus as defined in claim 1 further including a second fastener with a first end portion connectable with a bone portion and a second end portion extending through a second opening in said member, a second connecting ring for connecting said second fastener to said member, and a second clamping member engaging said second end of said second fastener and said second connecting ring to connect said second connecting ring to said member, said second connecting ring extending into said second opening in said member and having a passage with a longitudinal axis through which said second end portion of said second fastener extends, said second fastener being positionable in any one of a plurality of angular positions relative to said connecting ring so that said longitudinal axis of said second fastener extends at any one of a plurality of angles to said longitudinal axis of said passage in said second connecting ring, said second clamping member engaging said second end of said second fastener and said second connecting ring to connect said second connecting ring to said member and connect said second fastener in any one of said plurality of angular positions relative to said second connecting ring.

25. An apparatus as defined in claim 24 wherein said opening in said member is a first elongate slot, said connecting ring being positionable in any one of a plurality of positions along said first elongate slot relative to said member prior to said clamping member engaging said connecting ring, said second opening in said member being a second elongate slot, said second connecting ring being positionable in any one of a plurality of positions along said second elongate slot relative to said member prior to said second clamping member engaging said second connecting ring.

26. An apparatus as defined in claim 24 further including a third fastener with a first end portion connectable with a bone portion and a second end portion extending through a third opening in said member, a third connecting ring for connecting said third fastener to said member, and a third clamping member engaging said second end of said third fastener and said third connecting ring to connect said third connecting ring to said member, said third connecting ring extending into said third opening in said member and having a passage with a longitudinal axis through which said second end portion of said third fastener extends, said third fastener being positionable in any one of a plurality of angular positions relative to said third connecting ring so that said longitudinal axis of said third fastener extends at any one of a plurality of angles to said longitudinal axis of said passage in said third connecting ring, said third clamping member engaging said second end portion of said third fastener and said third connecting ring to connect said third connecting ring to said member and connect said third fastener in any one of said plurality of angular positions relative to said third connecting ring.

27. An apparatus as defined in claim 26 wherein said opening in said member is a first elongate slot, said connecting ring being positionable in any one of a plurality of positions along said first elongate slot relative to said member prior to said clamping member engaging said connecting ring, said second opening in said member being a second elongate slot, said second connecting ring being positionable in any one of a plurality of positions along said second elongate slot relative to said member prior to said second clamping member engaging said second connecting ring, said third opening in said member being a third elongate slot, said third connecting ring being positionable in any one of a plurality of positions along said third elongate slot relative to said member prior to said third clamping member engaging said third connecting ring.

28. An apparatus as defined in claim 27 wherein said member is a T-shaped plate.

29. An apparatus as defined in claim 1 wherein said member is connectable with a spinal rod extending along a spinal column.

30. An apparatus as defined in claim 29 wherein said member has a passage through which the spinal rod extends.

31. An apparatus as defined in claim 30 wherein said opening in said member is an elongate slot with a longitudinal axis extending transverse to a longitudinal axis of said passage in said member through which the spinal rod extends.

32. An apparatus as defined in claim 30 further including a fastener engageable with the spinal rod to clamp the spinal rod to said member.

33. An apparatus comprising:
a member connectable with a bone portion, said member having an elongate slot;
a fastener for connecting said member to the bone portion having a longitudinal axis, said fastener having a first end portion engageable with the bone portion and a second end portion extending through said elongate slot in said member;
a connecting ring for connecting said member to said fastener, said connecting ring extending into said elongate slot in said member and being positionable in any one of a plurality of positions along said elongate slot relative to said member, said connecting ring having a passage with a longitudinal axis through which said second end portion of said fastener extends, said fastener being positionable in any one of a plurality of angular positions relative to said connecting ring so that said longitudinal axis of said fastener extends at any one of a plurality of angles to said longitudinal axis of said passage in said connecting ring, said connecting ring having first and second portions engageable with each other to connect said connecting ring to said member, said second portion of said connecting ring extending into an opening in said first portion; and
a clamping member engaging said second end portion of said fastener and said connecting ring to connect said connecting ring to said member in any one of said plurality of positions relative to said member and connect said fastener in any one of said plurality of angular positions relative to said connecting ring.

34. An apparatus as defined in claim 33 wherein said fastener is universally pivotable in any direction relative to said connecting ring.

35. An apparatus as defined in claim 33 wherein said clamping member applies a force to said connecting ring to move said first portion of said connecting ring relative to a said second portion of said connecting ring, said first and second portions moving into engagement with said member to prevent movement of said connecting ring relative to said member.

36. An apparatus as defined in claim 33 wherein said connecting ring has surfaces engageable with surfaces on said member to prevent rotation of said connecting ring relative to said member.

37. An apparatus as defined in claim 36 wherein said connecting ring has projections engageable with grooves on said member to prevent rotation of said connecting ring relative to said member.

38. An apparatus as defined in claim 37 wherein said grooves on said member extend transverse to a longitudinal axis of said elongate slot.

39. An apparatus as defined in claim 37 wherein first and second portions of said connecting ring have projections engageable with grooves on said member to prevent rotation of said connecting ring relative to said member.

40. An apparatus as defined in claim 36 wherein said connecting ring has first surfaces extending parallel to each other, said member having first and second surfaces at least partially defining said elongate slot and extending parallel to each other, said first and second surfaces on said connecting ring engaging said first and second surfaces defining said elongate slot to prevent rotation of said connecting ring relative to said member.

41. An apparatus as defined in claim 33 wherein said connecting ring has a tapered surface defining said passage through which said second end portion of said fastener extends.

42. An apparatus as defined in claim 41 wherein said connecting ring has an arcuate surface engageable with an arcuate surface on said clamping member.

43. An apparatus as defined in claim 42 wherein said arcuate surface on said connecting ring is a convex surface and said arcuate surface on said clamping member is a concave surface.

44. An apparatus as defined in claim 42 wherein said fastener has an intermediate portion between said first and second end portions, said intermediate portion being engageable with said connecting ring.

45. An apparatus as defined in claim 44 wherein said connecting ring has an arcuate surface engageable with an arcuate surface on said intermediate portion of said fastener.

46. An apparatus as defined in claim 45 wherein said arcuate surface on said connecting ring is concave and said arcuate surface on said intermediate portion of said fastener is convex.

47. An apparatus as defined in claim 33 wherein said first and second portions of said connecting ring have an interference fit.

48. An apparatus as defined in claim 33 further including a second fastener having a first end portion engageable with a bone portion and a second end portion and a second clamping member engageable with said second end portion of said second fastener and said member for connecting said second fastener to said member, said second end portion of said second fastener extending through a second elongate slot in said member, said second fastener being universally pivotable in any direction relative to an end of said second elongate slot.

49. An apparatus as defined in claim 48 wherein said end of said elongate slot is defined by a tapered surface.

50. An apparatus as defined in claim 48 wherein said second fastener includes an intermediate portion between said first and second end portions, said intermediate portion having an arcuate surface engageable with an arcuate surface on said member.

51. An apparatus as defined in claim 50 wherein said arcuate surface on said intermediate portion is convex and said arcuate surface on said member is concave.

52. An apparatus as defined in claim 48 wherein said member includes an arcuate surface adjacent to said end of said second elongate slot, said second clamping member having an arcuate surface engageable with said arcuate surface on said member.

53. An apparatus as defined in claim 52 wherein said arcuate surface on said member is convex and said arcuate surface on said second clamping member is concave.

54. An apparatus as defined in claim 33 further including a second fastener with a first end portion connectable with a bone portion and a second end portion extending through a second elongate slot in said member, a second connecting ring for connecting said second fastener to said member, and a second clamping member engaging said second end portion of said second fastener and said second connecting ring to connect said second connecting ring to said member, said second connecting ring extending into said second elongate slot in said member and being positionable in any one of a plurality of positions along said second elongate slot relative to said member, said second connecting ring having a passage with a longitudinal axis through which said second end portion of said second fastener extends, said second fastener being positionable in any one of a plurality of angular positions relative to said connecting ring so that said longitudinal axis of said second fastener extends at any one of a plurality of angles to said longitudinal axis of said passage in said second connecting ring, said second clamping member engaging said second end of said second fastener and said second connecting ring to connect said second connecting ring to said member in any one of said plurality of positions along said second elongate slot and connect said second fastener in any one of said plurality of angular positions relative to said second connecting ring.

55. An apparatus as defined in claim 54 further including a third fastener with a first end portion connectable with a bone portion and a second end portion extending through a third elongate slot in said member, a third connecting ring for connecting said third fastener to said member, and a third clamping member engaging said second end of said third fastener and said third connecting ring to connect said third connecting ring to said member, said third connecting ring extending into said third elongate slot in said member and being positionable in any one of a plurality of positions along said third elongate slot relative to said member, said third connecting ring having a passage with a longitudinal axis through which said second end portion of said third fastener extends, said third fastener being positionable in any one of a plurality of angular positions relative to said third connecting ring so that said longitudinal axis of said third fastener extends at any one of a plurality of angles to said longitudinal axis of said passage in said third connecting ring, said third clamping member engaging said second end portion of said third fastener and said third connecting ring to connect said third connecting ring to said member in any one of said plurality of positions along said third elongate slot and connect said third fastener in any one of said plurality of angular positions relative to said third connecting ring.

56. An apparatus as defined in claim 55 wherein said member is a T-shaped plate.

57. An apparatus as defined in claim 33 wherein said member is connectable with a spinal rod extending along a spinal column.

58. An apparatus as defined in claim 57 wherein said member has a passage through which the spinal rod extends.

59. An apparatus as defined in claim 58 wherein said elongate slot has a longitudinal axis extending transverse to a longitudinal axis of said passage in said member through which the spinal rod extends.

60. An apparatus as defined in claim 55 further including a fastener engageable with the spinal rod to clamp the spinal rod to said member.

* * * * *

UNITED STATES PATENT AND TRADEMARK OFFICE
CERTIFICATE OF CORRECTION

PATENT NO. : 6,641,583 B2
DATED : November 4, 2004
INVENTOR(S) : Alan E. Shluzas and Gene P. DiPoto It is certified that error appears in the above-identified patent and that said Letters Patent is hereby corrected as shown below:

Column 9,
Line 26, after "claim" change "4" to -- 1 --.
Line 33, after "claim" change "5" to -- 1 --.
Line 37, after "claim" change "4" to -- 1 --.

Column 12,
Line 23, after "to" delete "a".
Line 32, after "claim" change "36" to -- 33 --.
Line 38, after "claim" change "37" to -- 33 --.
Line 38, after "wherein" insert -- said --.
Line 42, after "claim" change "36" to -- 33 --.

Column 14,
Line 47, after "claim" change "55" to -- 58 --.

Signed and Sealed this

Eleventh Day of January, 2005

JON W. DUDAS
*Director of the United States Patent and Trademark Office*